United States Patent
Van Hoonacker et al.

(10) Patent No.: US 9,395,372 B2
(45) Date of Patent: Jul. 19, 2016

(54) METHOD FOR COATING NANOPARTICLES

(75) Inventors: Anne Van Hoonacker, Zingem (BE); Meike Roskamp, Zellik (BE); Patrick Englebienne, Zingem (BE)

(73) Assignee: PHARMADIAGNOSTICS NV, Zellik (BE)

(*) Notice: Subject to any disclaimer, the term of this patent is extended or adjusted under 35 U.S.C. 154(b) by 0 days.

(21) Appl. No.: 13/877,774

(22) PCT Filed: Oct. 13, 2011

(86) PCT No.: PCT/EP2011/067894
§ 371 (c)(1),
(2), (4) Date: Apr. 4, 2013

(87) PCT Pub. No.: WO2012/049251
PCT Pub. Date: Apr. 19, 2012

(65) Prior Publication Data
US 2013/0196450 A1 Aug. 1, 2013

Related U.S. Application Data

(60) Provisional application No. 61/392,529, filed on Oct. 13, 2010.

(30) Foreign Application Priority Data

Oct. 13, 2010 (GB) .................................. 1017251.8
Mar. 10, 2011 (GB) .................................. 1104081.3

(51) Int. Cl.
*G01N 33/543* (2006.01)
*G01N 33/58* (2006.01)

(52) U.S. Cl.
CPC ........ *G01N 33/587* (2013.01); *G01N 33/54346* (2013.01)

(58) Field of Classification Search
CPC ..................... G01N 33/54346; G01N 33/587
USPC ......................................................... 436/525
See application file for complete search history.

(56) References Cited

U.S. PATENT DOCUMENTS 5,279,792 A * 1/1994 Moeremans et al. ......... 422/430
5,585,278 A 12/1996 Vunnam et al.
5,939,021 A * 8/1999 Hansen et al. ................ 422/400

(Continued)

FOREIGN PATENT DOCUMENTS

WO WO 01/88540 A1 11/2001
WO WO 01/89820 A2 11/2001

(Continued)

OTHER PUBLICATIONS

International Search Report for International Application No. PCT/EP2011/067894, mailed on Jan. 16, 2012.

(Continued)

*Primary Examiner* — Mark Shibuya
*Assistant Examiner* — Pensee Do
(74) *Attorney, Agent, or Firm* — Knobbe, Martens, Olson & Bear, LLP

(57) ABSTRACT

The invention relates to methods for coating nanoparticles with a limited amount of a binding partner and nanoparticles obtainable by the methods disclosed. In particular, the invention is of interest, when coating with only a limited amount of protein is desirable.

8 Claims, 10 Drawing Sheets

(56) References Cited

U.S. PATENT DOCUMENTS

| | | | |
|---|---|---|---|
| 5,945,293 A * | 8/1999 | Siiman et al. | 436/534 |
| 6,833,275 B1 | 12/2004 | Nichtl | |
| 2004/0058457 A1 * | 3/2004 | Huang et al. | 436/524 |
| 2006/0228554 A1 * | 10/2006 | Tan et al. | 428/404 |
| 2010/0029902 A1 | 2/2010 | Choi et al. | |

FOREIGN PATENT DOCUMENTS

| | | |
|---|---|---|
| WO | WO 2010/002479 A1 | 1/2010 |
| WO | WO 2010/006201 A2 | 1/2010 |
| WO | WO 2010/007857 A1 | 1/2010 |
| WO | WO 2010/052665 A2 | 5/2010 |

OTHER PUBLICATIONS

Wang et al., "Influence of surfactants on the morphology of $SnO_2$ nanocrystals prepared via a hydrothermal method," *Journal of Solid State Chemistry*, vol. 189, pp. 49-56 (Abstract) (May 1, 2012).

Batteiger et al., "The Use of Tween 20 as a Blocking Agent in the Immunological Detection of Proteins Transferred to Nitrocellulose Membranes," *Journal of Immunological Methods*, vol. 55, pp. 297-307 (1982).

* cited by examiner

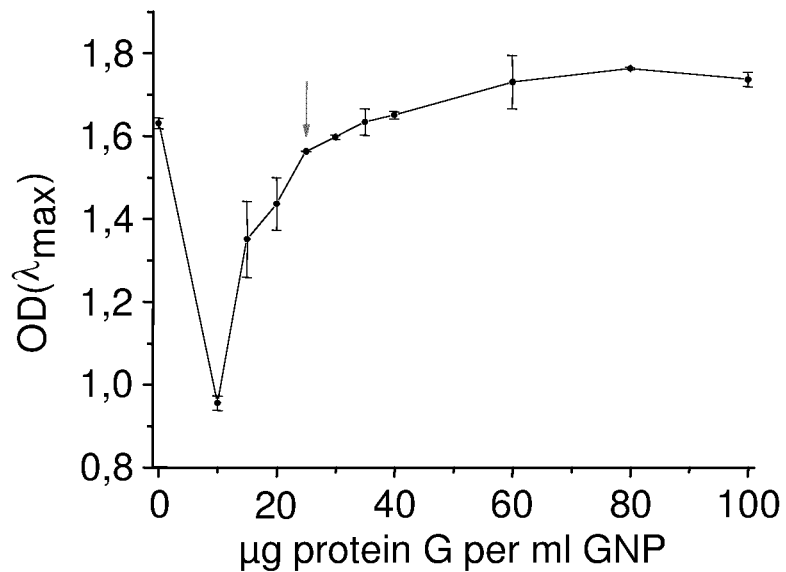
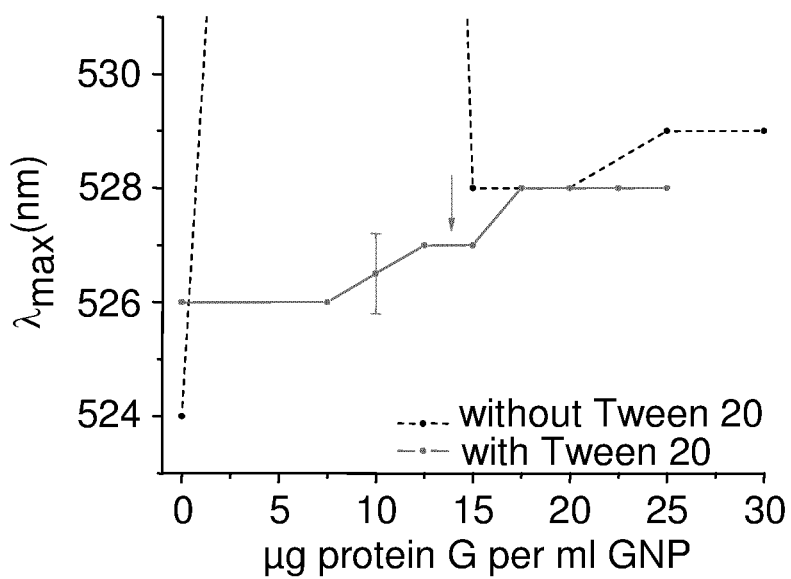

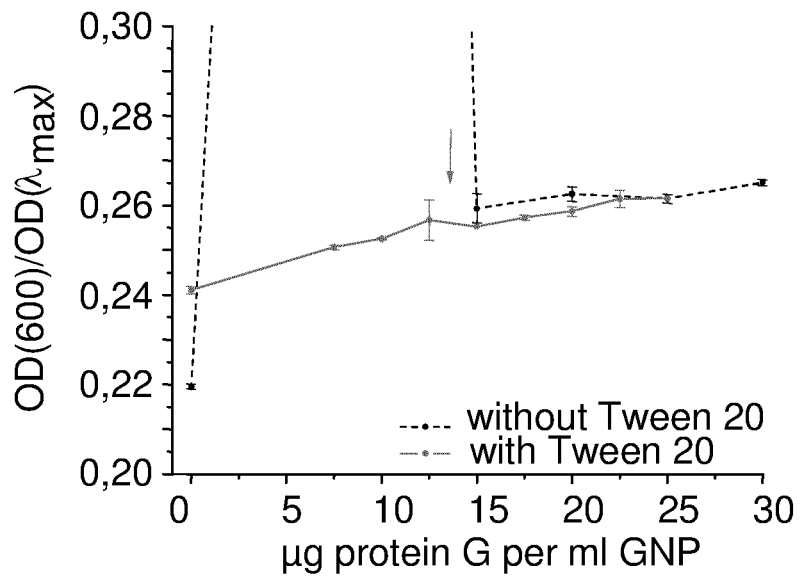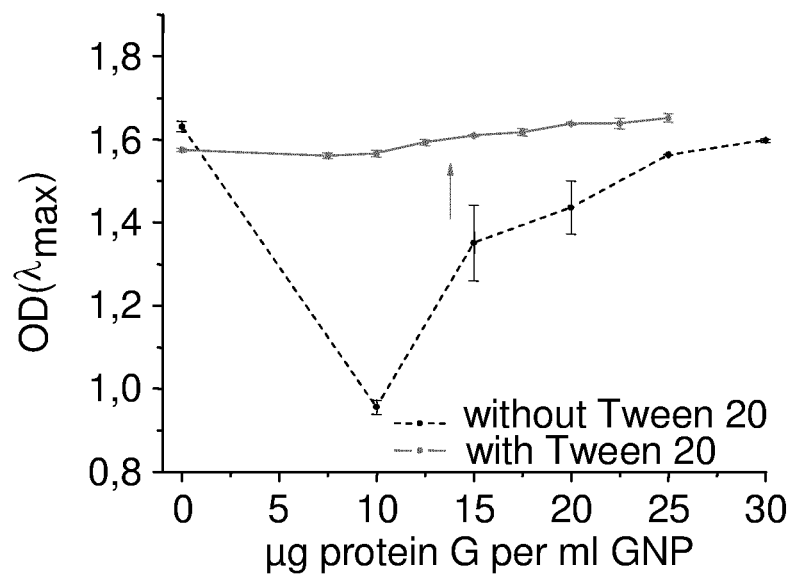

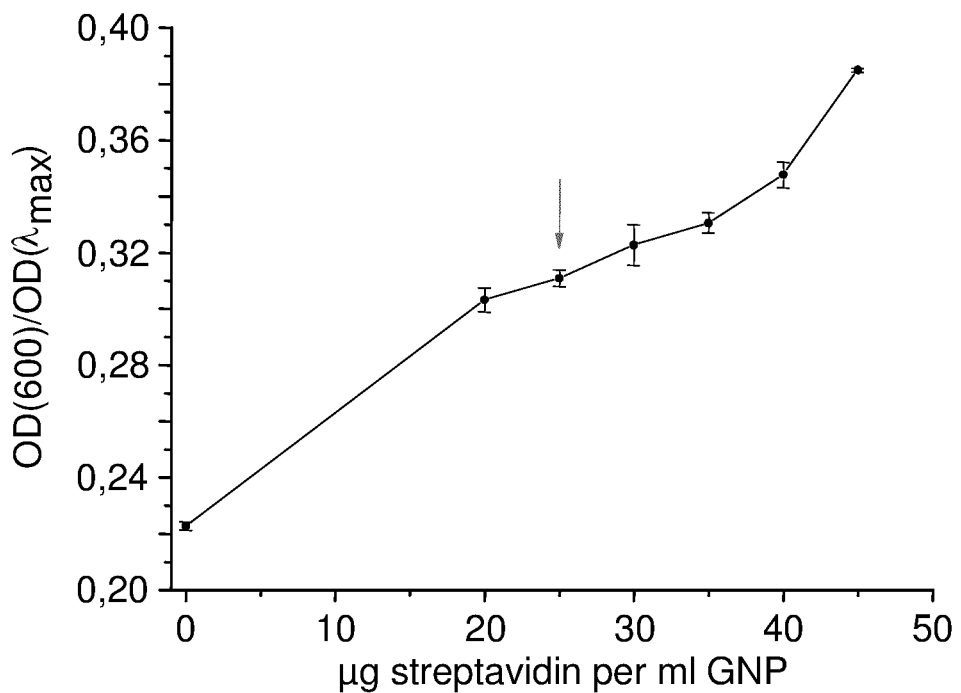
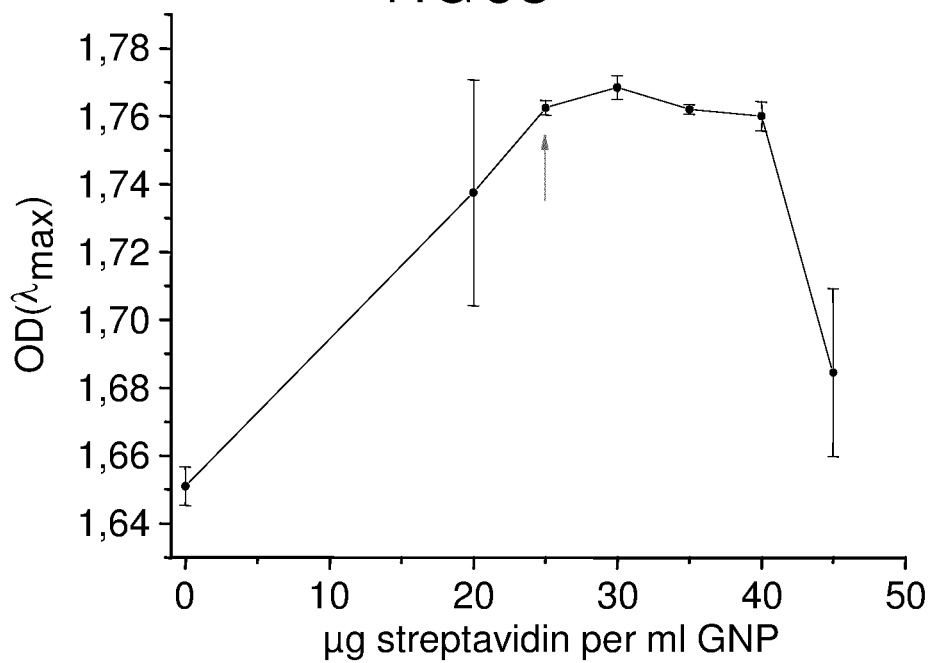

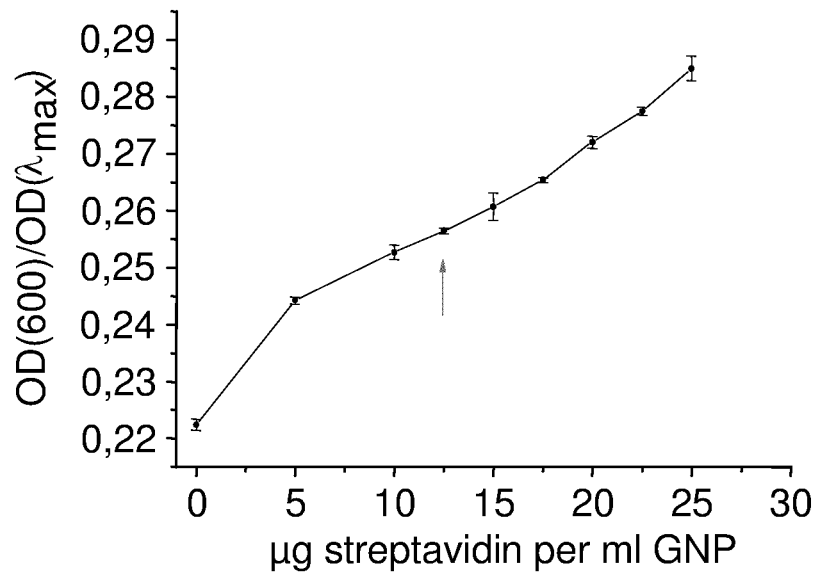
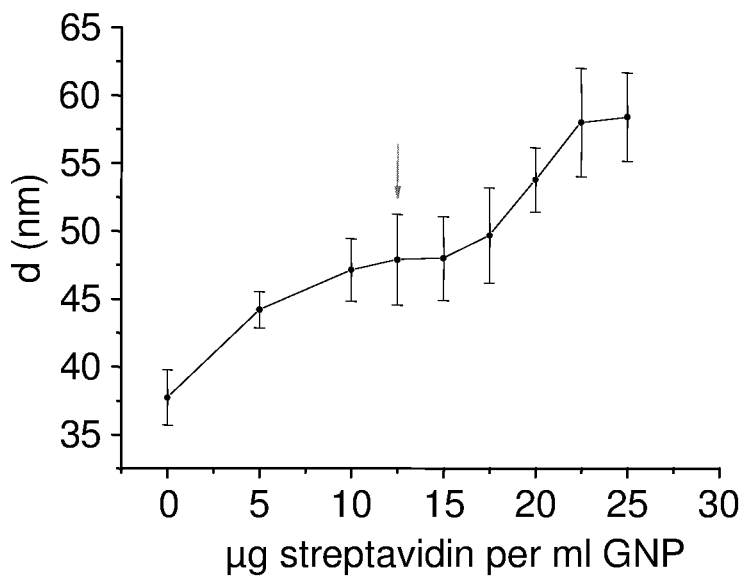

METHOD FOR COATING NANOPARTICLES

CROSS-REFERENCE TO RELATED APPLICATIONS

This application is the U.S. National Phase under 35 U.S.C. §371 of International Application PCT/EP2011/067894, filed Oct. 13, 2011, which claims priority to U.S. Provisional Application No. 61/392,529, filed Oct. 13, 2010, GB Application No. 1017251.8, filed Oct. 13, 2010 and GB Application No. 1104081.3, filed Mar. 10, 2011.

FIELD OF THE INVENTION

The present invention relates to a method for coating nanoparticles with a binding partner, whereby a reduced amount of binding partner is required. In specific embodiments, the invention provides methods for coating nanoparticles with a single layer of a binding partner such as a protein. In particular, the invention is directed to a method for coating nanoparticles with a single layer of protein, wherein only low amounts of protein are required.

BACKGROUND OF THE INVENTION

Nanoparticles are nowadays extensively used in many applications in both medical and biomedical sciences such as for drug delivery, for therapy and for diagnostics. For many of these applications, nanoparticles are coated with proteins. Nanoparticles coated with proteins such as antibodies to cancer cells can be used for instance to locate cancer cells in the body. Similarly, for analyte detection in vitro, probes such as antibodies are bound to nanoparticles, whereby binding of the analyte to the antibody on the nanoparticle is detected.

More in particular metal nanoparticles coated with proteins can be used to transduce binding events by changes in their absorption at least in the visible light spectrum. This phenomenon of Localised Surface Plasmon Resonance (LSPR) enables the screening of interactions of biomolecules. Thus, metal nanoparticles coated with proteins can be used in the detection of antibody-ligand interactions, receptor-ligand interactions, enzyme-ligand binding and antibody-antigen association-dissociation kinetics.

Nanoparticles coated with binding partners such as proteins have been described in the art, as well as methods for coating nanoparticles. For instance, US 2010/0029902 describes a method for coating nanoparticles which comprises mixing the nanoparticles and one or more protein types with a dispersed solution, wherein the proteins are adsorbed to entire surfaces of the nanoparticles in order to control and prevent aggregation of the nanoparticles.

A disadvantage of prior art methods is the requirement of high amounts of the binding partner to completely coat the nanoparticles. Often, only low amounts of the binding partner of interest are available.

In addition, as some of these prior art methods result in nanoparticles coated with multiple layers of the binding partner, the interaction of the bound protein with another compound occurs at an increased distance from the surface of the nanoparticle, which affects signal strength in detection methods.

There remains a need in the art to provide methods for coating nanoparticles with binding partners such as proteins wherein only low amounts of the binding partner are required and, for particular embodiments, wherein coating with a single layer of the binding partner can be achieved.

SUMMARY OF THE INVENTION

The present inventors have found a method for coating nanoparticles which involves the use of a limited amount of binding partner. Moreover, the inventors have found methods which allow, where of interest coating with a single layer of the binding partner. Thus, the methods of the invention overcome one or more of the above-mentioned problems of the prior art.

In a first aspect, the invention relates to methods for coating nanoparticles with a binding partner, wherein the methods comprise concentrating the binding partner at the surface of the nanoparticle. In particular embodiments the method involves ensuring a concentration of the binding agent near the nanoparticle. In particular embodiments of the invention, the methods involve ensuring an electrostatic interaction between the nanoparticle and the binding agent.

In particular embodiments, the invention relates to methods for coating nanoparticles with a binding partner, wherein the methods comprise contacting said nanoparticles with a nonionic, cationic and/or zwitterionic detergent prior to or upon contacting the nanoparticles with a solution of said binding partner.

The inventors have found that the methods described herein enable the coating of nanoparticles with a limited amount of the binding partner. Moreover, in particular embodiments the methods can be used to obtain a single layer of a binding agent, such as a protein using low amounts of the binding agent. These methods are therefore advantageous, because often e.g. only small amounts of the protein of interest are available. Furthermore, in particular embodiments, the methods of the present invention allow controlling the thickness of the protein layer on the nanoparticles. For instance, in particular embodiments the methods enable the production of stable nanoparticles coated with only one layer of protein on the nanoparticle surface. This is of particular interest, e.g. when further coating of the nanoparticles with another molecule is intended, as the distance of this molecule to the nanoparticle surface is reduced. Moreover, if the interaction between the coated protein and another compound is to be studied, the distance of this interaction to the surface of the nanoparticle is reduced, thereby improving the optical detection of the interaction.

In addition, in particular embodiments, the methods of the present invention are advantageous when coating at high pH values is required. In the absence of a nonionic, cationic and/or zwitterionic detergent, the adjustment to high pH values might lead to agglutination of the nanoparticles. Particular embodiments of the above-described methods may also be advantageous when the solution of the binding agent needs to be buffered. In the absence of a nonionic, cationic and/or zwitterionic detergent, even small salt concentrations in the solution might lead to agglutination of the nanoparticles, more particularly where the binding agent is a protein. If the nanoparticles are contacted with a nonionic, cationic and/or zwitterionic detergent prior to (and optionally during) coating, no agglutination occurs, even in the presence of moderate salt concentrations. Yet another advantage of particular embodiments of the methods of the present invention is that a homogenous coating can be ensured, even when the protein is a protein or a small peptide in a low amount. Furthermore, particular embodiments of the above-described method may also be advantageous when the binding agent is a protein which is aggregated before coating. Incubation of the protein with a nonionic, cationic and/or zwitterionic detergent before coating will help to stabilize the protein in a non-aggregated form, thereby improving the coating result.

In particular embodiments, the present invention relates to methods which comprise the step of mixing a solution comprising the nanoparticles with a solution comprising the binding agent, wherein said solution comprising the nanoparticles and/or said solution comprising the binding agent comprises said nonionic, cationic and/or zwitterionic detergent. The methods of the present invention further comprise contacting the solution comprising the nanoparticles with the solution comprising the binding agent with each other so as to ensure an interaction between said binding agent and said nanoparticle. In further particular embodiments, the methods according to the invention further comprise a step of ensuring the binding of said nanoparticle with said binding agent.

In particular embodiments, the step of contacting the solution comprising the nanoparticle with the solution comprising the binding agent ensures the binding of said nanoparticle with said binding agent. In particular embodiments, the binding agent is a protein and said method involves contacting said nanoparticle with said protein in the presence of a solution comprising the nanoparticles and/or said solution comprising the proteins comprises said nonionic, cationic and/or zwitterionic detergent, thereby allowing the protein to form a single layer on the surface of said nanoparticles.

In particular embodiments, the present invention provides methods which further comprises, prior to the coating of said nanoparticles, the step of determining the minimal amount of protein required for obtaining stable nanoparticles in the presence of said nonionic, cationic and/or zwitterionic detergent.

In particular embodiments, the present invention relates to methods as described above, wherein said nonionic detergent is selected from the group comprising polysorbates, octylphenol ethoxylates, glucamines, lubrol, Brij®, Nonidet®, Pluronic®, Genapol® and Igepal®.

In particular embodiments, the present invention provides methods as described above, wherein said cationic detergent is selected from hexadecyltrimethyl ammonium bromide (CTAB) or trimethyl(tetradecyl) ammonium bromide (TTAB).

In particular embodiments, the present invention relates to methods as described above, wherein said zwitterionic detergent is selected from the group comprising amidosulfobetaines, alkylbetaines and ammonio propanesulfonates.

In particular embodiments, the present invention provides methods as described above, wherein said nonionic, cationic and/or zwitterionic detergent concentration ranges between 0.0001 and 1 volume/volume %.

In particular embodiments, the present invention relates to methods as described above, wherein the amount of protein used in the coating is higher than the minimal amount of protein required for obtaining stable nanoparticles.

In particular embodiments, the present invention provides methods as described above, wherein said nanoparticles comprise a conductive polymer colloid, a noble metal colloid, a metal/conductive polymer composite colloid, silica or latex.

In particular embodiments, the present invention relates to methods as described above, wherein said nanoparticles comprise a transition metal selected from the group comprising Au, Ag, Cu, Ta, Pt, Pd, and Rh and preferably wherein said transition metal is gold, silver or copper.

In particular embodiments, the present invention relates to nanoparticle compositions comprising nanoparticles obtainable by one or more of the methods as described above.

In particular embodiments, the present invention relates to kits comprising nanoparticles and instructions for coating said nanoparticles with any of the methods as described above.

In particular embodiments, the present invention provides kits as described above, which further comprise a nonionic, cationic and/or zwitterionic detergent or a solution comprising a nonionic, cationic and/or zwitterionic detergent.

In particular embodiments, the present invention provides methods for localized surface plasmon resonance detection of the interaction of a compound with a protein bound to a nanoparticle, which method comprises coating said nanoparticle with a binding agent such as but not limited to a protein with any of the methods as described above.

BRIEF DESCRIPTION OF THE DRAWINGS

The invention will now be described, inter alia with reference to the accompanying Figures, which are provided by way of example only and should not be considered to limit the scope of the present invention.

FIGS. 1 and 2 demonstrate the effect of the nonionic detergent Tween 20 on the amount of protein G required to stabilize gold nanoparticles (GNP), according to a particular embodiment of the invention.

FIG. 1 demonstrates the results of the concentration titration of protein G in the absence of Tween 20. The arrow indicates the lowest amount of protein G that stabilizes the GNP. FIG. 1C represents a plot of OD($\lambda_{max}$) against the amount of protein G per ml GNP.

FIG. 2 demonstrates the results of the concentration titration of protein G in the presence of Tween 20. The arrow indicates the lowest amount of protein G that stabilizes the GNP. FIG. 2A represents a plot of $\lambda_{max}$ against the amount of protein G per ml GNP. FIG. 2B represents a plot of OD(600)/OD($\lambda_{max}$) against the amount of protein G per ml GNP. FIG. 2C represents a plot of OD($\lambda_{max}$) against the amount of protein G per ml GNP.

FIGS. 3 and 4 demonstrate the effect of Tween 20 on the amount of streptavidin required to stabilize gold nanoparticles (GNP), according to a particular embodiment of the invention.

FIG. 3 demonstrates the results of the concentration titration of streptavidin in the absence of Tween 20. The arrow indicates the lowest amount of streptavidin that stabilizes the GNP. FIG. 3B represents a plot of OD(600)/OD($\lambda_{max}$) against the amount of streptavidin per ml GNP. FIG. 3C represents plot of OD($\lambda_{max}$) against the amount of streptavidin per ml GNP.

FIG. 4 shows the results of the concentration titration of streptavidin in the presence of Tween 20. The arrow indicates the lowest amount of streptavidin that stabilizes the GNP in the presence of Tween 20. FIG. 4C represents a plot of OD($\lambda_{max}$) against the amount of streptavidin per ml GNP. FIG. 4D represents a plot of the hydrodynamic diameter of the GNP against the amount of streptavidin per ml GNP.

FIG. 5 shows the results of the concentration titration of Tween 20 coated GNP with protein G, according to a particular embodiment of the invention. The arrow indicates the lowest amount of protein G that stabilizes the Tween 20 coated GNP.

FIG. 6 shows the results of the concentration titration of Tween 20 coated GNP with protein A, according to a particular embodiment of the invention. The arrow indicates the lowest amount of protein A that stabilizes the Tween 20 coated GNP.

DETAILED DESCRIPTION OF THE INVENTION

Figure 1A:
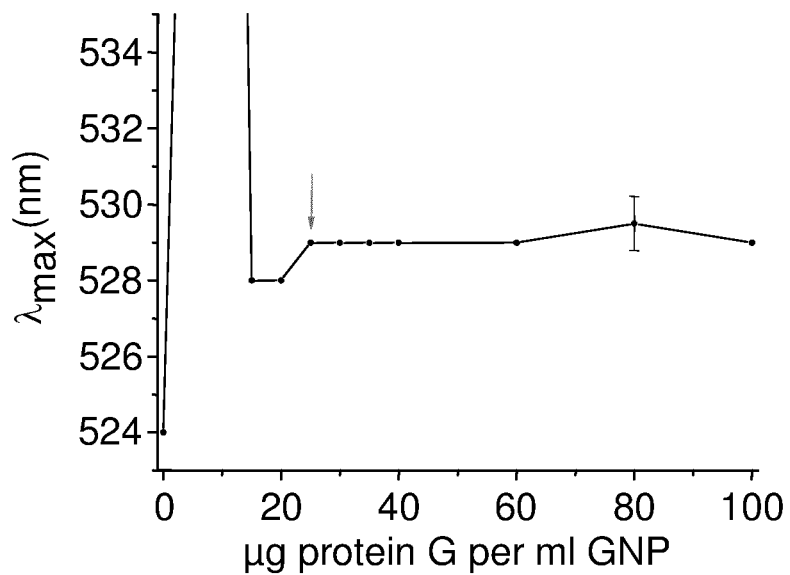
FIG. 1A represents a plot of $\lambda_{max}$ against the amount of protein G per ml GNP.

In the following passages, different aspects of the invention are described in more detail.

Each aspect so described may be combined with any other aspect or aspects unless clearly indicated to the contrary. In particular, any feature indicated as being preferred or advantageous may be combined with any other feature or features indicated as being preferred or advantageous.

In the context of the present invention, the terms used are to be construed in accordance with the following definitions, unless a context dictates otherwise.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where embodiments are referred to as "comprising" particular features, elements or steps, this is intended to specifically include embodiments which consist of the listed features, elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The present invention relates to methods for coating nanoparticles with a binding agent wherein a reduced amount of binding agent is required. More particularly, the invention provides methods wherein an interaction between the nanoparticle and the binding agent is ensured prior to or during the coating step. In particular embodiments, the interaction ensures an efficient coating of the nanoparticle. In further embodiments, the methods may involve covalent binding of the binding agent to the nanoparticle after concentration of the binding agent at the surface of the nanoparticle.

The term binding agent as used herein refers to a molecule of interest which is to be coated onto a nanoparticle and which itself can ensure binding to another entity. Typically the binding partner is a member of a specific known or envisaged binding pair or couple such as antigen-antibody, receptor-ligand, enzyme-ligand, sugar-lectin, receptor-receptor binding agent, protein-oligonucleotide, etc. In particular embodiments, the binding partner is a protein or a peptide. In further particular embodiments the binding partner contains at least 5 amino acids, more particularly at least 10, at least 20, at least 50 amino acids or more.

In one aspect, the invention provides methods for coating nanoparticles, wherein only low amounts of protein are required, and to single-layered nanoparticles obtained by these methods.

According to this aspect the invention relates to methods for coating nanoparticles with a protein, wherein the methods comprise contacting said nanoparticles with a nonionic, cationic and/or zwitterionic detergent prior to or upon contacting the nanoparticles with a solution of said protein.

The term "nonionic detergent" as used herein refers to a detergent which does not have any ionic groups. In embodiments of the methods of the invention, the nonionic detergent is selected from the group comprising polysorbates, octylphenol ethoxylates, glucamines, Iubrol, Brij®, Nonidet®, Pluronic®, Genapol® and Igepal®. In particular embodiments, the polysorbate is chosen from the group comprising polysorbate 20, polysorbate 40, polysorbate 60, polysorbate 65, polysorbate 80 and polysorbate 85. In particular embodiments, the octylphenol ethoxylate is selected from the group comprising TRITON® X-15, TRITON® X-35, TRITON® X-45, TRITON® X-100, TRITON® X-102, TRITON® X-114, TRITON X-165 (70%), TRITON® X-305 (70%), TRITON® X-405 (70%) and TRITON® X-705 (70%). In particular embodiments, the glucamine is selected from the group comprising of N-octanoyl-N-methylglucamine (MEGA-8), N-nonanoyl-N-methylglucamine (MEGA-9) and N-decanoyl-N-methylglucamine (MEGA-10).

The term "cationic detergent" as used herein refers to a detergent with a positive ionic charge. In embodiments of the methods of the invention, the cationic detergent is selected from hexadecyltrimethyl ammonium bromide (CTAB) or trimethyl(tetradecyl) ammonium bromide (TTAB).

The term "zwitterionic detergent" as used herein refers to a detergent which has ionic groups, but no net charge. In embodiments of the methods of the invention, the zwitterionic detergent is selected from the group comprising amidosulfobetaines, alkylbetaines and ammonio propanesulfonates. In preferred embodiments, the zwitterionic detergent is selected from the group comprising amidosulfobetaine-14, amidosulfobetaine-16, 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), 3-(4-heptyl)phenyl-3-hydroxypropyl)dimethylammoniopropanesulfonate (C7BzO), EMPIGEN® BB, 3-(N,N-dimethyloctylammonio) propanesulfonate inner salt, 3-(decyldimethylammonio) propanesulfonate inner salt, 3-(dodecyldimethylammonio) propanesulfonate inner salt, 3-(N,N-dimethylmyristylammonio) propanesulfonate inner salt, 3-(N,N-dimethylpalmitylammonio) propanesulfonate inner salt, 3-(N,N-dimethyloctadecylammonio) propanesulfonate inner salt.

It will be understood to the skilled person that reference herein to the use of a nonionic, cationic and/or zwitterionic detergent includes the use of combinations of different nonionic, cationic and/or zwitterionic detergents.

In particular embodiments of the methods of the invention, the detergent is a nonionic detergent.

The methods of the present invention are characterized in that the nanoparticles are contacted with the nonionic, cationic and/or zwitterionic detergent prior to or during coating with the protein of interest. Indeed, nonionic, cationic and/or zwitterionic detergents have been used in the prior art in buffers upon manipulation of coated nanoparticles. However, according to the methods of the present invention, the nanoparticles are contacted with a nonionic, cationic and/or zwitterionic detergent prior to or during the coating process, such as to improve the coating process.

The concentration of nonionic, cationic and/or zwitterionic detergent used is not critical, but typically ranges between 0.0001 and 1 volume/volume %. Particularly, the nonionic, cationic and/or zwitterionic detergent may be used in a concentration ranging between 0.005 and 0.5 volume/volume %. Preferably, the nonionic, cationic and/or zwitterionic detergent may be used in a concentration ranging between 0.001 and 0.1 volume/volume %. More preferably, the nonionic, cationic and/or zwitterionic detergent concentration may be 0.001, 0.002, 0.005, 0.01, 0.02, 0.03, 0.04, 0.05, 0.06, 0.07, 0.08, 0.09 or 0.1 volume/volume %, or a value in the range between any two of the aforementioned values.

In particular embodiments, the binding agent is a protein and the invention provides methods which allow the coating of a nanoparticle with a single layer of protein and nanoparticles obtainable by these methods. In particular, in these embodiments, the invention provides methods for coating nanoparticles with a single layer of protein. In these embodiments, the methods comprise the step of mixing a solution comprising nanoparticles with a solution comprising proteins, thereby allowing the proteins to form a single layer on the surface of said nanoparticles, wherein said solution comprising nanoparticles and/or said solution comprising proteins comprises said nonionic, cationic and/or zwitterionic detergent.

In the methods of the present invention, it is envisaged that the nanoparticles can be contacted with the nonionic, cationic and/or zwitterionic detergent prior to contacting the nanoparticles with the protein, or simultaneously. Accordingly, in one embodiment, the invention provides methods wherein the solution comprising the protein comprises the nonionic, cationic and/or zwitterionic detergent. This may in particular embodiments have the advantage that the proteins are stabilized. Thereafter, the nanoparticles are contacted with the solution or suspension comprising the proteins and the nonionic, cationic and/or zwitterionic detergent.

In other embodiments, the methods of the invention comprise preparing a solution comprising the nanoparticles and adding a nonionic, cationic and/or zwitterionic detergent thereto. In these embodiments, the nanoparticles are contacted with the nonionic, cationic and/or zwitterionic detergent prior to contacting them with the protein solution. The methods then comprise mixing the solution comprising the proteins with the solution comprising the nanoparticles and the nonionic, cationic and/or zwitterionic detergent.

These embodiments of the methods of the present invention are envisaged to generally improve the coating of nanoparticles with proteins. The nature of the protein is not critical to this aspect of the invention and thus can be any size and includes, but is not limited to, antibodies or fragments thereof, antigens, enzymes or substrates, receptors or ligands etc. The term proteins thus includes peptides.

The inventors have found that in this aspect of the invention, the methods are of particular interest for the coating of nanoparticles with proteins which are susceptible to hydrophobic interactions and/or proteins that will easily aggregate on low ionic strength. More particularly, the methods of the present invention are advantageous for the coating of proteins which are susceptible to hydrophobic interactions at salt concentrations of less than 10 mM or for the coating of proteins that do not support such a low ionic strength and must be conjugated at higher ionic strength to maintain their activity and/or conformation. Typically proteins susceptible to hydrophobic interactions comprise non-polar groups which mutually repel water and other polar groups, resulting in a net attraction of the non-polar groups for each other. It is known that proteins comprising hydrocarbon alkyl groups on ala, val, leu, and ile and/or benzene (aromatic) rings on phe and tyr are often susceptible to hydrophobic interactions. Examples of such proteins are proteins associated with the cellular membrane and proteins involved in transport functions. The invention is illustrated herein with streptavidin, protein G and protein A. Accordingly, in particular embodiments, the proteins as used in the methods of the present invention are proteins susceptible to hydrophobic interactions at low salt concentrations. Accordingly particular embodiments of the methods for coating nanoparticles with a protein comprise a coating step performed in the presence of higher salt concentration. While the term higher salt concentration is typically dependent on the protein of interest, this typically involves salt concentrations of more than 10 mM, more particularly more than 50 mM, most particularly more than 100 mM. In further particular embodiments the methods of the present invention involve the coating of proteins having a pI of 9 or more, preferably of 10 or more. The term "pI" refers here to the isoelectric point of the protein, being the pH at which the protein or its surface carries no net electrical charge.

In particular embodiments, the methods of the present invention comprise the step of determining the hydrophobicity of the protein before mixing the solution comprising the nanoparticles with the solution comprising the proteins. The hydrophobicity of a protein can be determined by calculating a hydropathicity plot as a function of the amino acid sequence of the protein or by hydrophobic interaction chromatography or reversed phase chromatography.

In alternative embodiments, the methods of the present invention include the step of contacting the binding agent with the nanoparticle in the presence of a nonionic, cationic and/or zwitterionic detergent, so as to ensure a concentration of the binding agent at the surface of the nanoparticle and a step of ensuring the binding of the binding agent to the surface of the nanoparticle. In further particular embodiments the step of ensuring the binding of the binding agent to the surface of the nanoparticle is performed by activation of functional groups (for example carboxyl groups) on the nanoparticles, thereby making them reactive against the binding partner (for example amines). In particular embodiments the ligand is an amine-containing molecule such as a protein or peptide and the binding to the nanoparticle is ensured by activation of a carboxyl group on the nanoparticle.

Is envisaged that the methods of the present invention are of particular interest when the binding agent is a protein. This will be illustrated herein below.

It is envisaged that particular embodiments of the methods of the present invention are of interest when coating of the protein at high pH values is required. In the absence of a nonionic, cationic and/or zwitterionic detergent, the adjustment to high pH values might lead to agglutination of the nanoparticles. According to particular embodiments, the methods of the present invention comprise coating the protein in nonionic, cationic and/or zwitterionic detergent at a high pH, and adjusting the pH after coating.

It is further envisaged that particular embodiments of the methods of the present invention are of particular interest when the protein solution needs to be buffered, but is susceptible to agglutination even at low salt concentrations. According to particular embodiments, the methods of the present invention comprise contacting the nanoparticles with the protein solution in the presence of moderate salt concentrations and a nonionic, cationic and/or zwitterionic detergent.

In order to ensure optimal coating in the methods of the present invention it may be of interest to contact the nanoparticles with specific amounts of the protein of interest. As indicated above, the methods of the present invention are particularly advantageous in that they allow coating with a minimal amount of protein. Nevertheless, in particular embodiments it is envisaged that the protein amount required to coat the surfaces of the nanoparticles is to be determined.

Accordingly, in particular embodiments, the invention provides methods for coating nanoparticles, wherein the method further comprises, prior to the coating of said nanoparticles, the step of determining the minimal amount of protein required for obtaining stable nanoparticles in the presence of said nonionic, cationic and/or zwitterionic detergent. The step of determining the optimal protein amount for coating the surface of the nanoparticles is typically performed by a concentration titration. The nanoparticles are mixed with different amounts of protein and absorption spectra are recorded. For instance, in particular embodiments, nanoparticles are mixed with increasing amounts of protein typically in the range from 0 to 1000 µg of protein per ml of nanoparticles.

In particular embodiments, the step of determining concentration titration encompasses that after an incubation time of typically 10 min, a salt is added (e.g. NaCl, 1 M) and after another 10 min, absorption spectra of these samples are recorded between 350 and 900 nm. The minimal amount of protein necessary to stabilize the nanoparticles can be determined using plots of $\lambda_{max}$, $OD(\lambda_{max})$ and/or the ratio $OD(600)/OD(\lambda_{max})$ against the protein amount per ml nanoparticles. The lowest protein amount, where all plots show the highest similarity to the blank is the protein amount necessary to stabilize the particles. In alternative embodiments, the step concentration titration encompasses adding the protein to the nanoparticles in different concentrations directly (without addition of salt) whereby the spectrum is read e.g. after 30 min.

In particular embodiments, the methods of the present invention may comprise the step of determining the optimal protein amount for coating of the nanoparticles. In general, the optimal amount of protein (usually expressed as protein concentration, e.g. µg/ml) for coating of the nanoparticles will depend on the structure and molecular weight of the protein. For larger proteins the relative weight of protein vs. particles will decrease. In particular embodiments, the amount of proteins used is higher than said minimal amount of protein required for obtaining stable nanoparticles. In a further embodiment, the amount of proteins used is higher than the amount of protein adsorbable to the entire surfaces of the nanoparticles.

The methods of the present invention further allow controlling of the coating by a discrete amount of protein of interest (i.e. the protein intended for coating and used in further applications, e.g. for interaction with another compound, see below). This can be achieved inter alia by performing the methods of the present invention and using either compositions comprising only the protein of interest or compositions of the protein combined with a protein which is not reactive for the purposes intended (in the further application of the coated nanoparticle).

In the present application, reference to "protein" or "proteins" is generally intended to refer to the protein of interest. However, in particular embodiments this refers to a combination of protein of interest and unreactive protein, more particularly in well-defined proportions. In these embodiments, it is possible to further reduce and control the amount of protein of interest coated on the nanoparticle.

In particular embodiments, the methods of the present invention may further comprise a step of controlling the adsorption and/or the binding of the proteins to the nanoparticles. This can be performed by different detection methods, including but not limited to optical detection methods. In particular embodiments, the binding of the protein to the nanoparticle is checked by detecting a shift in localized surface plasmon resonance (LSPR) wavelength. As used herein, the term "localized surface plasmon resonance" or "LSPR" relates to methods which detect optical changes at the surface of nanoparticles made from noble metals. When the metal surfaces of the nanoparticles are excited by electromagnetic radiation, they exhibit collective oscillations of their conduction electrons, known as localized surface plasmons (LSPs). When excited in this fashion, the nanoparticles act as nanoscale antennas, concentrating the electromagnetic field into very small volumes adjacent to the nanoparticles. Exceptionally large enhancements in electromagnetic intensity can be obtained this way. The nanoparticles used in the LSPR enable the occurrence of the resonance oscillations. The term "absorbance" refers to the extent to which a sample absorbs light. In LSPR changes in absorbance may be measured providing an indication of through monitoring changes in the refractive index. Intensity and wavelength of maximum absorbance can be detected for the LSPR extinction band.

The methods of the present invention are generally applicable to the coating of nanoparticles, which can be of any suitable material or shape, such as for instance, but not limited to, nanoparticles, nanobeads, nanospheres, nanopyramids, nanowires, nanoprisms, nanocubes, nanorods, mesh etc. One of skill in the art will appreciate that other nanostructures may also be useful in the present invention. In particular embodiments, the nanoparticles are round nanostructures. In further particular embodiments, the nanoparticles have a diameter ranging between 1 and 1000 nm, particularly between 25 and 750 nm, more particularly between 50 and 500 nm. The diameter of the nanoparticles may be for instance 50, 75, 100, 150, 200, 250, 300, 350, 400, 450 or 500 nm, or any value in the range between any two of the aforementioned values. In particular embodiments, the nanoparticles are nanorods. In further embodiments, the nanorods have an aspect ratio (i.e. length divided by width) ranging between 1.1 and 10, more particularly between 1.5 and 5. In certain embodiments, the nanorods have a width or diameter between 2 and 10 nm. In particular embodiments, the nanorods have a length between 4 and 45 nm.

The method of present invention may be performed with any type of colloidal particles able to be coated by electrostatic interactions. In particular embodiments, the nanoparticles used in the context of the present invention comprise a metal, a conductive polymer colloid, a noble metal colloid, a metal/conductive polymer composite colloid, silica or latex.

The term "colloid", as used herein, refers to a fluid composition of microscopic nanoparticles suspended in a liquid medium. The term "conductive polymer" refers to an electrically conductive polymeric material. In an embodiment, conductive polymers are organic polymers, or PI-conjugated organic polymers. For example, conductive polymers may be polypyrroles such as polypyrrole, poly(N-substituted pyrrole), poly(3-substituted pyrrole), and poly(3,4-disubstituted pyrrole); polythiophenes such as polythiophene, poly(3-substituted thiophene), poly(3,4-disubstituted thiophene), and polybenzothiophene; polyisothianaphthenes such as polyisothianaphthene; polythienylenevinylenes such as polythienylenevinylene; poly(p-phenylenevinylenes) such as poly(p- phenylenevinylene); polyanilines such as polyaniline, poly (N-substituted aniline), poly(3-substituted aniline), and poly(2,3-substituted aniline); polyacetylenes such as polyacetylene; polydiacetylenes such as polydiacetylene; polyazulenes such as polyazulene; polypyrenes such as polypyrene; polycarbazoles such as polycarbazole and poly(N-substituted carbazole), polyselenophenes such as polyselenophene; polyfurans such as polyfuran and polybenzofuran; poly(p-phenylens) such as poly(p-phenylene); polyindoles such as polyindole; polypyridazines such as polypyridazine; polyacenes such as naphthacene, pentacene, hexacene, heptacene, dibenzopentacene, tertabenzopentacene, pyrene, dibenzopyrene, chrysene, perylene, coronene, Terylene, ovalene, quoterylene, and circumanthracene; derivatives (such as triphenodioxazine, triphenodithiazine, hexacene-6, 15-quinone) which are prepared by substituting some of carbon atoms of polyacens with atoms such as N, S, and O, or a functional group such as a carbonyl group; polymers such as polyvinylcarbazoles, polyphenylenesulfide, and polyvinylenesulfide. In a particular embodiment, conductive polymers are polypyrrole, polythiophene, polyaniline or their derivatives.

As is known in the art, the conducting polymer may be doped by incorporating into the polymer, materials having a functional group such as a dimethylamino group, a cyano group, a carboxyl group and a nitro group, materials such as benzoquinone derivatives, and tetracyanoethylene as well as tetracyanoquinodimethane, and derivatives thereof, which work as an acceptor which accepts electrons, or, for example, materials having a functional group such as an amino group, an alkyl group, a hydroxyl group, an alkoxy group, and a phenyl group; substituted amines such as phenylenediamine; anthracene, benzoanthracene, substituted benzoanthracenes, pyrene, substituted pyrene, carbazole and derivatives thereof, and tetrathiafulvalene and derivatives thereof, which work as a donor which is an electron donor. The term "doping", as used herein, means that electron accepting molecules (acceptors) or electron donating molecules (donors) are incorporated in the polymer chain. When the doping agent is a substituent group to the monomer used to synthesize the polymer, the term self-doping polymer is used. In other cases, the doping agent is external and included after synthesis in the polymer chain (usually as a film), such as iodine vapor. In the present invention, both acceptors and donors may be employed as doping agents.

The term "metal colloid", as used herein, refers to a colloid in which the suspended microscopic nanoparticles are metal nanoparticles. The term "noble metal" refers to Group VIII metals of the Periodic Table including, but not limited to: platinum, iridium, palladium and the like, as well as gold, silver etc.

The term "metal/conductive polymer composite colloid", as used herein, refers to a colloid made up of metal nanoparticles having a conductive polymer present on a surface thereof.

In particular embodiments, the nanoparticles used in the context of the present invention comprise one or more metals selected from Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au and/or Ac. One of skill in the art will appreciate that the transition metals described above can each adopt several different oxidation states, all of which are useful in the present invention. In some instances, the most stable oxidation state is formed, but other oxidation states are useful in the present invention. In addition, the transition metals of the present invention can be metal oxides. In an embodiment, the invention relates to a method, wherein said nanoparticles comprise a transition metal selected from the group comprising Au, Ag, Cu, Ta, Pt, Pd, and Rh and preferably wherein said transition metal is gold, silver or copper.

As detailed above in particular embodiments, the coating methods according to the invention rely on electrostatic interactions between the binding agents, more particularly the protein molecules, and the nanoparticles. However, for certain applications more stable protein-nanoparticle conjugates may be required. Such stable conjugates can be obtained via covalent coupling between protein molecules and the nanoparticles. In order to ensure such a covalent coupling, the surface of the nanoparticles is usually provided with functional groups, such as for example carboxyl or amine groups or peptides, or azides or alkenes, etc. In a typical protocol for covalent attachment according to the prior art, a first step in the covalent coupling is the activation of the functional groups, e.g. carboxyl groups, on the nanoparticles, thereby making them reactive against the binding partner, e.g. a protein. Then the binding partner is added. Typically, an excess of the binding partner is needed to achieve complete coverage of the nanomaterial with the binding partner. After completion of the coupling reaction, the excess of binding partner is removed by purification.

However, according to particular embodiments of the present invention optimized coating methods are provided involving the covalent attachment of proteins to nanoparticles. Indeed, in particular embodiments, the coating method according to the present invention ensures the formation of a protein monolayer around the nanoparticles, thereby providing a close contact between the protein and any (activated) functional groups on the nanoparticles, thus concentrating the protein at the surface of the nanoparticle and accelerating the formation of the covalent bond. In contrast with the methods for covalent attachment known in the art is that with the method according to the present invention, little or no protein excess is required.

Accordingly, in particular embodiments, the surface of the nanoparticles is functionalized with one or more functional groups. Methods for functionalization of nanoparticles are well known to the skilled person, and may for example involve attachment of ligands to the nanoparticle surface, wherein said ligands comprise at least one linking agent having a first portion linked to the nanoparticle and a second portion which is a functional group capable of linking to an affinity molecule, e.g. a protein. In particular embodiments, the surface of the nanoparticles is functionalized with one or more functional groups selected from the group consisting of a carboxyl, an amine, polyethylene glycol, a peptide, DNA and RNA. Carboxyl groups are especially useful for binding proteins, because the carboxyl group can react with an amine moiety of a protein, thereby forming an amide bond. Accordingly, in specific embodiments, the functional groups comprise carboxyl groups. In particular embodiments, the functional groups are activated prior to or upon contacting the nanoparticles with a solution comprising the protein. Activation of functional groups is well known to the skilled person. If the functional group is a carboxyl, the carboxyl may be activated using one or more carboxyl activating groups. Examples of useful carboxyl activating groups include, but are not limited to, carbodiimide reagents, phosphonium reagents such as benzotriazolyloxy-tris-(dimethylamino) phosphonium hexafluorophosphate (BOP) and the like, uronium or carbonium reagents such as O-(benzotriazol-l-yl)-N,N',N'-tetramethyluronium hexafluorophosphate (HBTU), N-hydroxy-succinimide (NHS), benzotriazol-1-yl-oxy-tripyrrolidinophosphonium hexafluorophosphate (PyBOP)

and the like; 1-ethoxycarbonyl-2-ethoxy-1,2-dihydroqunoline (EEDQ); 1-methyl-2-chloropyridinium iodide (Mukaiyama's reagent) and the like.

In a further aspect, the invention relates to a nanoparticle composition comprising nanoparticles obtainable by one or more of the methods of the present invention.

Indeed, in particular embodiments, the methods of the present invention provide a unique way of obtaining nanoparticles which are coated with a single layer of protein. The thickness of the protein layer can be determined by measuring the hydrodynamic diameter of the particles through dynamic light scattering (DLS) measurements. An increase in the hydrodynamic diameter is equivalent to an increase in the protein layer thickness. Nanoparticles coated with a single layer of protein provide a number of advantages. Coating of protein-coated nanoparticles with another compound is improved, because the distance of this compound to the nanoparticle surface is reduced. Furthermore, if the interaction between the coated protein and another compound is to be studied, the distance to the surface of the nanoparticle is reduced, thereby improving the optical detection of the protein interactions by LSPR. According to particular embodiments, the invention provides nanoparticle compositions comprising nanoparticles coated with one or more proteins, wherein the one or more proteins are coated as a single layer on the nanoparticle.

In a further aspect, the invention provides kits comprising nanoparticles and further components and/or instructions for coating of the nanoparticles with protein according to one or more of the methods of the present invention. In particular embodiments, the kits according to the present invention comprise nanoparticles in solution, wherein said solution comprises a nonionic, cationic and/or zwitterionic detergent. Additionally or alternatively, the kits according to the present invention comprise nanoparticles and a separate nonionic, cationic and/or zwitterionic detergent or a separate solution comprising a nonionic, cationic and/or zwitterionic detergent. In particular embodiments, the kits comprise instructions for coating the nanoparticles according to the methods of the present invention.

A further aspect of the present invention relates to the use of the coated nanoparticles obtained according to the present invention in different applications. Indeed, the nanoparticles obtained by the coating methods of the present invention can be used in all known prior art applications involving protein-coated nanoparticles, including, but not limited to drug delivery, therapy, diagnostics, analyte-detection methods, targeting methods, etc.

Moreover it has been found that the nanoparticles obtained by particular embodiments of the methods of the present invention have particular advantages in specific applications. Indeed it is observed that for the optical detection of interactions of a first protein with a second compound (including a second protein) using nanoparticles, it is of interest that the interaction occurs as close as possible to the surface of the nanoparticle. Thus, coating of the first protein in a single layer on the nanoparticle surface ensures optimal detection of the interaction of said protein with another compound or protein. In particular embodiments, the coated nanoparticles of the present invention are used in analyte detection methods. In particular embodiments, the coating methods are optical detection methods, more particularly methods involving the detection of light scattering by the nanoparticle. In further particular embodiments, the nanoparticles obtainable or obtained by the methods of the present invention are used in LSPR detection methods.

LSPR detection methods are typically used in the context of measuring interactions between a first and a second compound, in the context of determining specific properties of one or both of the compounds or specific properties of the interaction between both compounds. In the methods of the present invention, the first compound, which is bound to the nanoparticle is a protein. In particular embodiments, the first and second compounds are a member of a specific known or envisaged binding pair or couple. Thus, the second compound (or potential cognate ligand) refers to a compound which may potentially interact with the first compound coupled to the nanoparticle. Typically the first compound and second compound are both sensing moieties which are members of a binding couple such as antigen-antibody, receptor-ligand, enzyme-ligand, sugar-lectin, receptor-receptor binding agent, and others. In these embodiments, the LSPR detection methods may serve for sensing the interaction between the two members of the binding pair.

The present invention is illustrated by the following non-limiting examples

EXAMPLES

Example 1

Contacting Nanoparticles with a Nonionic Detergent Upon Coating of the Nanoparticles with Protein G First the amount of protein G necessary to stabilize a certain volume of gold nanoparticles (GNP) in the absence of any nonionic, cationic and/or zwitterionic detergent has to be determined by a concentration titration. A solution made of GNP of 30 nm in diameter with an OD 4 at maximum wavelength contains $6 \times 10^{11}$ GNP/ml. The GNP are mixed with different amounts of protein in a typical range of 0 to 100 µg of protein per ml GNP. After an incubation time of 10 min, NaCl (1 M in $H_2O$) is added and after another 10 min, absorption spectra of these samples are recorded between 350 and 900 nm. To identify the smallest protein amount necessary to stabilize the nanoparticles three plots are made; $\lambda_{max}$, $OD(\lambda_{max})$ and the ratio $OD(600)/OD(\lambda_{max})$ are plotted against the protein amount per ml GNP. The lowest protein concentration, where all three plots show the highest similarity to the blank is the minimal protein amount necessary to stabilize the nanoparticles.

Figure 1B:
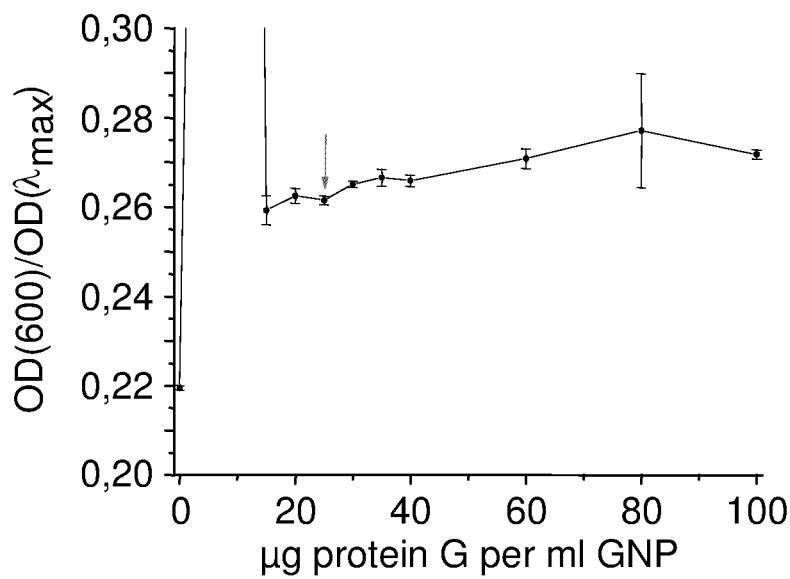
FIG. 1B represents a plot of OD(600)/OD($\lambda_{max}$) against the amount of protein G per ml GNP.

Particularly, the ratio $OD(600)/OD(\lambda_{max})$ should be as small as possible. A small shift of $\lambda_{max}$ to higher wavelengths and thereby a small increase in $OD(600)/OD(\lambda_{max})$ after coating with protein can be expected. Mostly, the $OD(\lambda_{max})$ also increases or decreases a bit. By concentration titration a protein amount of 25 µg protein G per ml GNP was determined to be the lowest amount that stabilizes the nanoparticles (FIG. 1).

After determining the minimal protein amount necessary to stabilize the nanoparticles in the absence of any nonionic, cationic and/or zwitterionic detergent, a concentration titration in the presence of a nonionic, cationic and/or zwitterionic detergent is performed. In the present examples, the nonionic detergent Tween 20 is used at a final concentration of 0.05%. The highest protein amount tested in the Tween 20 titration is the lowest amount of protein that stabilizes the nanoparticles in the absence of any nonionic, cationic and/or zwitterionic detergent. The titration is performed similarly to the concentration titration in the absence of any nonionic, cationic and/or zwitterionic detergent except that the protein is mixed with a fixed amount of Tween 20 before the addition of GNP. Absorption spectra of these samples are recorded and again the following three plots are made; $\lambda_{max}$, OD($\lambda_{max}$) and the ratio OD(600)/OD($\lambda_{max}$) are plotted against the protein amount per ml GNP.

Due to the Tween 20, all samples are stable after addition of NaCl (1 M in H$_2$O). The binding of the protein on the nanoparticle surface can be monitored by the development of $\lambda_{max}$ with increasing protein amount per ml GNP. The more protein is bound to the surface of the nanoparticles the more $\lambda_{max}$ shifts to higher wavelengths. This development also has an effect on the plot of OD(600)/OD($\lambda_{max}$). With increasing $\lambda_{max}$ the ratio OD(600)/OD($\lambda_{max}$) also slightly increases.

Figure 2D:
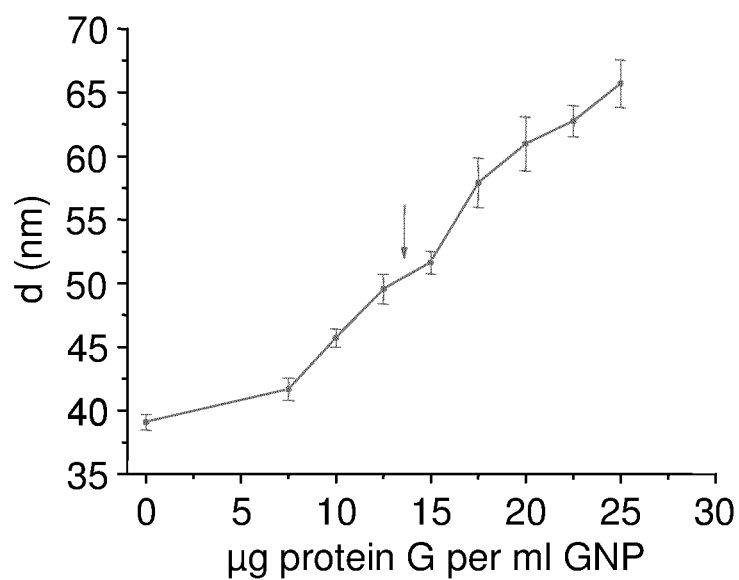
FIG. 2D represents a plot of the hydrodynamic diameter of the GNP against the amount of protein G per ml GNP.

The results of the concentration titration in the presence of Tween 20 are shown in FIG. 2. In addition to absorption spectra (FIG. 2A, 2B, 2C), dynamic light scattering (DLS) measurements were performed for every sample (FIG. 2D). An amount of 12.5 to 15 µg of protein G per ml GNP is enough to cover the nanoparticles with approximately one layer of protein G (FIG. 2, indicated by arrows). Two plateaus corresponding respectively to a first and a second layer of protein on the nanoparticles can be clearly identified (FIG. 2D). The use of 12.5 µg protein G per ml GNP, which is necessary to stabilize the nanoparticles in the presence of Tween 20, results in nanoparticles with a protein layer thickness of 5 nm. The use of 25 µg protein G per ml GNP, which is necessary to get stable nanoparticles in the absence of any nonionic, cationic and/or zwitterionic detergent, results in nanoparticles with a layer thickness of 12.5 nm, which is more than twice that big (FIG. 2D). The use of Tween 20 in the coating process thus enables to produce stable protein G coated GNP with only one layer of protein on the nanoparticle surface. Thereby it halves the necessary amount of protein G per ml GNP and if further coating of the nanoparticles with another molecule is intended, the distance of this molecule to the nanoparticle surface is reduced.

Comparison of the development of $\lambda_{max}$ (FIG. 2A) and the hydrodynamic diameter (FIG. 2D) of the nanoparticles with increasing protein amount shows that the development of the protein layer thickness with increasing protein amount can also be deduced from the plot of $\lambda_{max}$ against the protein amount per ml GNP. An increase of the hydrodynamic diameter, which is equivalent to an increase in the protein layer thickness, results in a slight red shift of $\lambda_{max}$. Given that DLS measurements are time consuming the opportunity to use only absorption spectra to get information about the thickness of the protein layer significantly reduces the time needed to determine the optimal protein amount for coating.

Example 2

Figure 3A:
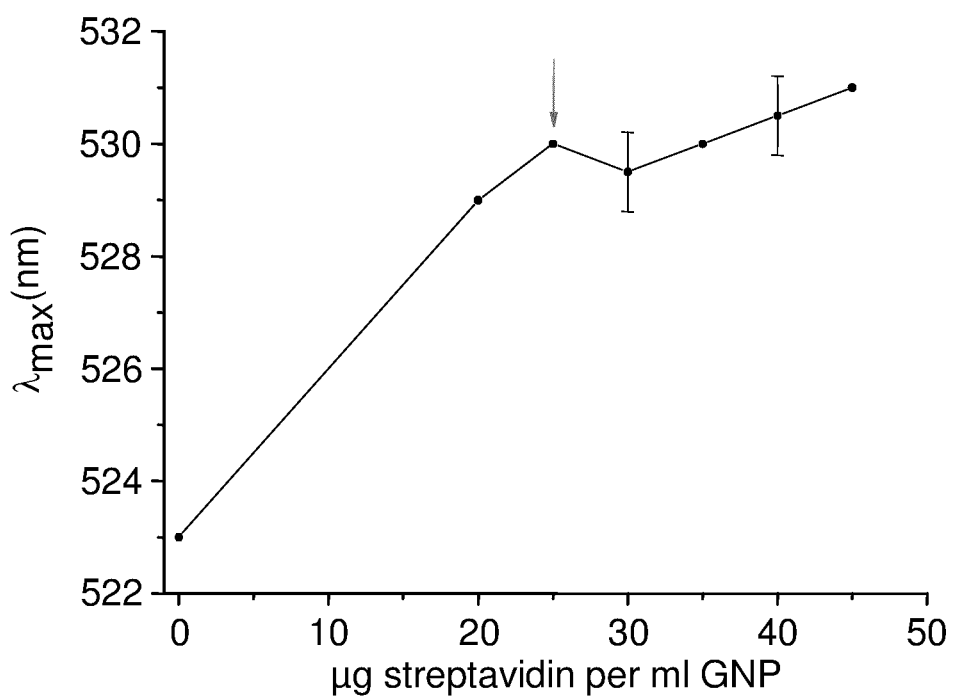
FIG. 3A represents a plot of $\lambda_{max}$ against the amount of streptavidin per ml GNP.
Figure 4A:
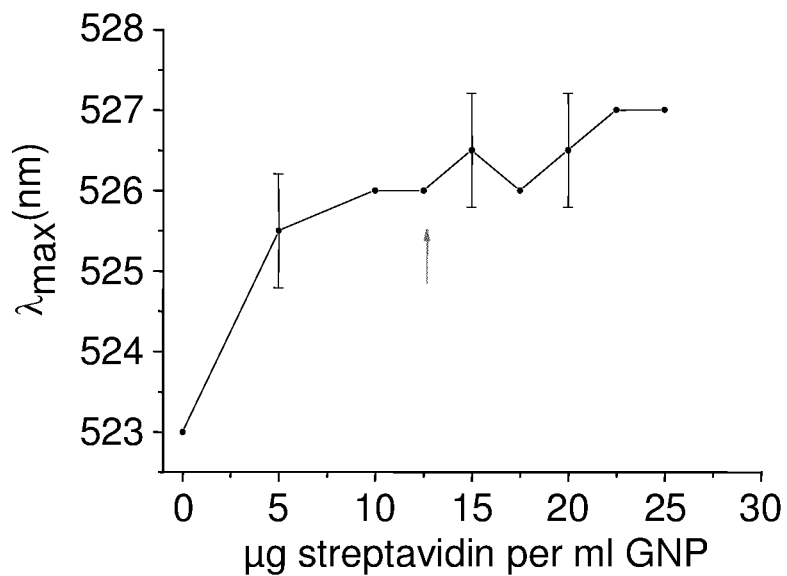
FIG. 4A represents a plot of $\lambda_{max}$ against the amount of streptavidin per ml GNP.
Figure 4B:
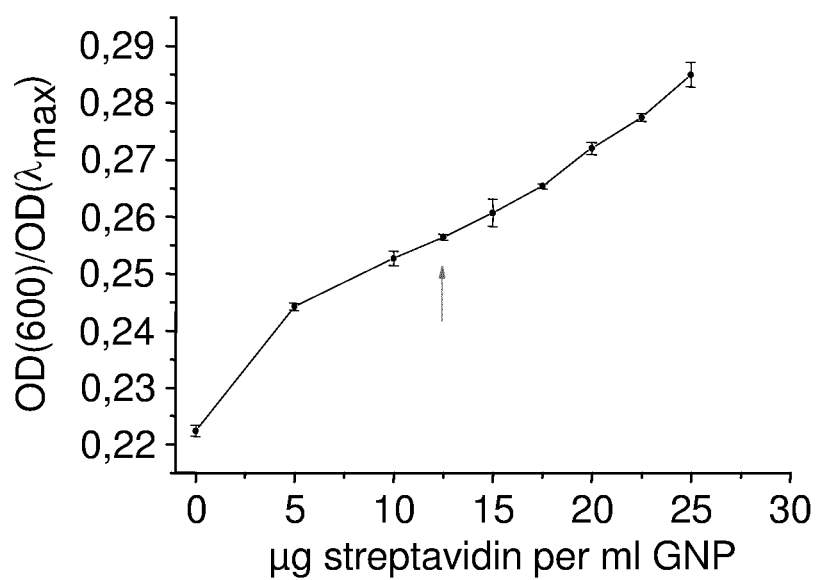
FIG. 4B represents a plot of OD(600)/OD($\lambda_{max}$) against the amount of streptavidin per ml GNP.

Contacting Nanoparticles with a Nonionic Detergent Upon Coating of the Nanoparticles with Streptavidin By concentration titration a protein amount of 25 µg streptavidin per ml GNP was determined to be the lowest amount that still stabilizes the nanoparticles in the absence of any nonionic, cationic and/or zwitterionic detergent (FIG. 3). In FIG. 4 the results of the adjacent concentration titration of streptavidin in the presence of Tween 20 are shown. An amount of 12.5 µg of streptavidin per ml GNP is needed to cover the nanoparticles with approximately one layer of streptavidin (FIG. 4). The use of 25 µg streptavidin per ml GNP, which is necessary to get stable nanoparticles in the absence of any nonionic, cationic and/or zwitterionic detergent, results in nanoparticles with a layer thickness which is twice that big (FIG. 4D). The DLS measurements presented in FIG. 4D clearly show the development of two subsequent protein layers which confirm the spectroscopic data presented in FIGS. 4A, 4B and 4C. Therefore, the method of the present invention halves the necessary amount of streptavidin per ml GNP.

Example 3

Contacting Nanoparticles with a Nonionic Detergent Prior to Coating of the Nanoparticles with Protein G Example 3 is similar to Example 1 except that the Tween 20 is added to the nanoparticles before the protein is added.

First the minimal protein amount that is necessary to coat a certain volume of GNP in the absence of any nonionic, cationic and/or zwitterionic detergent has to be determined. As already described in Example 1, a protein amount of 25 µg protein G per ml GNP was determined to be the lowest amount that still stabilizes the nanoparticles in the absence of Tween 20 (FIG. 1).

Figure 5A:
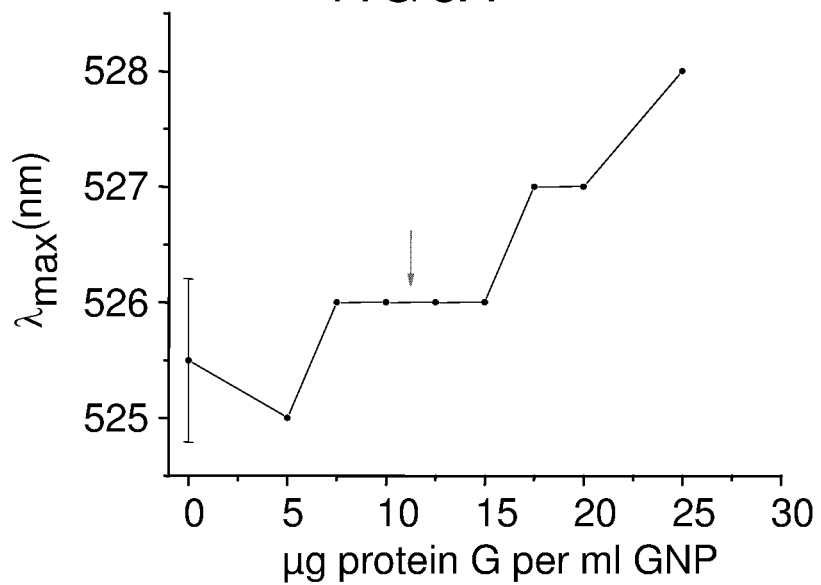
FIG. 5A represents a plot of $\lambda_{max}$ against the amount of protein G per ml GNP.
Figure 5B:
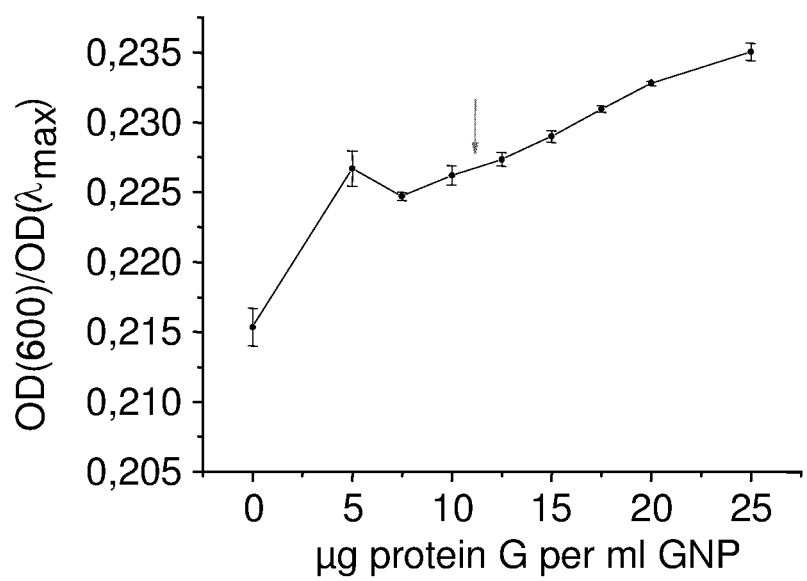
FIG. 5B represents a plot of OD(600)/OD($\lambda_{max}$) against the amount of protein G per ml GNP.
Figure 5C:
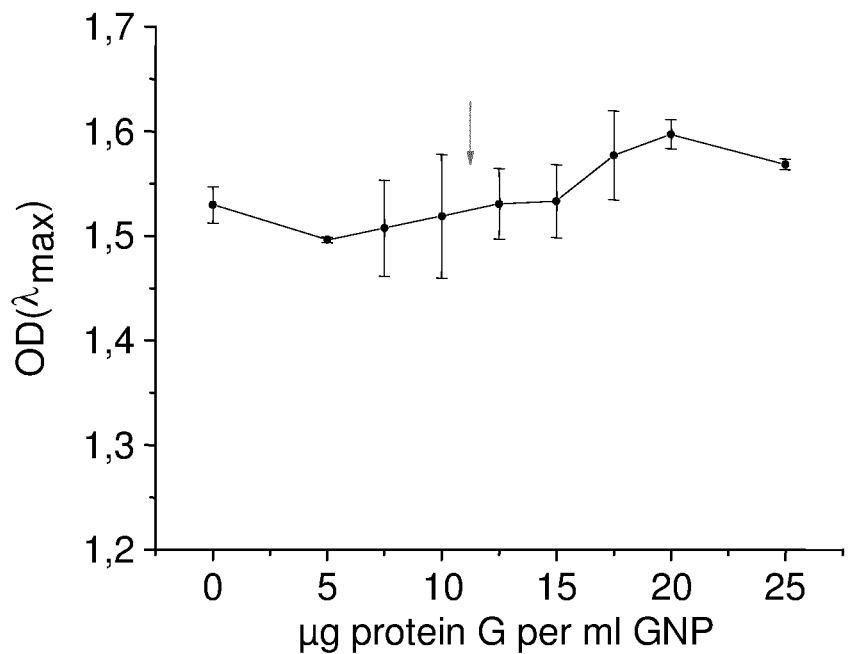
FIG. 5C represents a plot of OD($\lambda_{max}$) against the amount of protein G per ml GNP.

Then a concentration titration with Tween 20 coated GNP is performed. The highest protein amount tested in this titration is again the lowest amount of protein that stabilizes the nanoparticles in the absence of Tween 20. In contrast to Example 1, the GNP are coated with Tween 20 before the titration starts. The titration is performed similarly to the concentration titration in the absence of any nonionic, cationic and/or zwitterionic detergent except that Tween 20 stabilized nanoparticles are used instead of citrate coated GNP. The use of Tween 20 stabilized nanoparticles allows the progressive replacement of the nonionic detergent with the protein. This is advantageous when the protein to be coated is a small peptide or is buffered. Absorption spectra of these samples were recorded and the results of the concentration titration with Tween 20 coated GNP are shown in FIG. 5. An amount of 7.5 to 15 µg of protein G per ml GNP is needed to cover the nanoparticles with approximately one layer of protein G (FIG. 5). Compared to the 25 µg protein G per ml GNP that are needed to synthesize stable protein G coated GNP in the absence of Tween 20 this again is a significant reduction of protein amount per nanoparticle. This result is comparable to the result obtained in Example 1, considering that another colloid batch was used for this titration.

Example 4

Figure 6A:
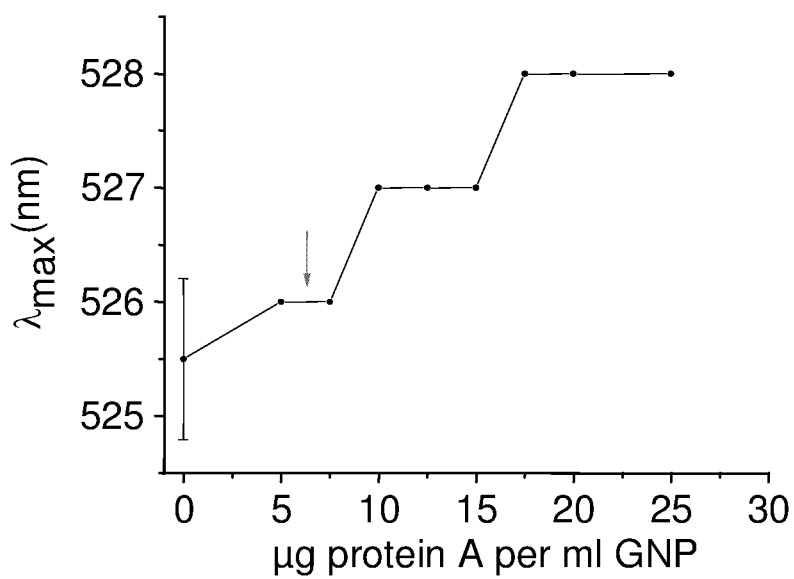
FIG. 6A represents a plot of $\lambda_{max}$ against the amount of protein A per ml GNP.
Figure 6B:
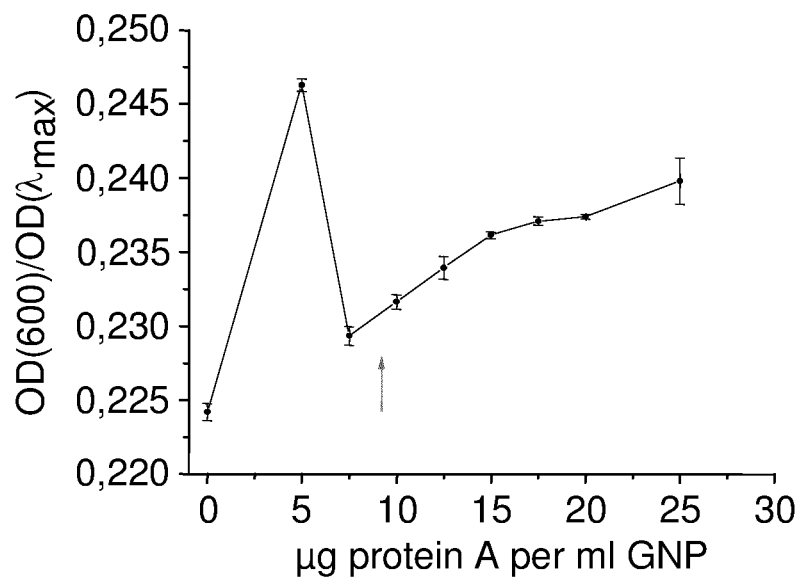
FIG. 6B represents a plot of OD(600)/OD($\lambda_{max}$) against the amount of protein A per ml GNP.
Figure 6C:
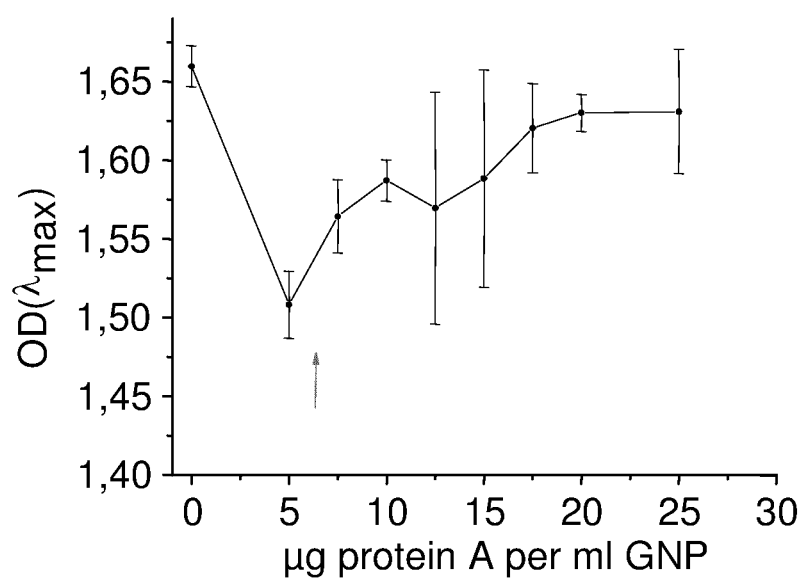
FIG. 6C represents a plot of OD($\lambda_{max}$) against the amount of protein A per ml GNP.

Contacting Nanoparticles with a Nonionic Detergent Prior to Coating of the Nanoparticles with Protein A In FIG. 6 the results of a concentration titration of Tween 20 coated GNP with protein A are shown. An amount of 5 to 7.5 µg of protein A per ml GNP is needed to cover the nanoparticles with approximately one layer of protein A.

What is claimed is:
1. A method for coating colloidal nanoparticles with a binding agent, wherein said colloidal nanoparticles are coated with a single layer of said binding agent and with a minimal amount of binding agent, and wherein the method comprises the steps of:
  determining the minimal amount of binding agent required for obtaining stable colloidal nanoparticles via concentration titration, wherein said determining of the minimal amount of binding agent is performed in the presence of a nonionic, cationic and/or zwitterionic detergent, and
  mixing a solution comprising the colloidal nanoparticles with a solution comprising said minimal amount of binding agent, wherein said solution comprising the col- loidal nanoparticles and/or said solution comprising the binding agent comprises said nonionic, cationic and/or zwitterionic detergent.

2. The method according to claim 1, wherein said nonionic detergent is selected from the group comprising polysorbates, octylphenol ethoxylates, and glucamines.

3. The method according to claim 1, wherein said cationic detergent is selected from hexadecyltrimethyl ammonium bromide (CTAB) or trimethyl(tetradecyl) ammonium bromide (TTAB).

4. The method according to claim 1, wherein said zwitterionic detergent is selected from the group comprising amidosulfobetaines, alkylbetaines and ammonio propanesulfonates.

5. The method according to claim 1, wherein said nonionic, cationic and/or zwitterionic detergent concentration ranges between 0.0001 and 1 volume/volume %.

6. The method according to claim 1, wherein said nanoparticles comprise a transition metal selected from the group comprising Au, Ag, Cu, Ta, Pt, Pd, and Rh.

7. The method according to claim 1, which further comprises activating a functional group on the surface of said nanoparticle, so as to ensure covalent binding of said binding agent on said surface.

8. The method according to claim 1, wherein said binding agent is a protein.

* * * * *